United States Patent [19]
Townes et al.

[11] Patent Number: 5,849,688
[45] Date of Patent: Dec. 15, 1998

[54] TRANSGENIC, CROSS-LINKED HEMOGLOBIN

[75] Inventors: Tim M. Townes; Steven L. McCune, both of Birmingham, Ala.

[73] Assignee: The UAB Research Foundation, Birmingham, Ala.

[21] Appl. No.: 816,118

[22] Filed: Mar. 11, 1997

Related U.S. Application Data

[60] Division of Ser. No. 100,465, Jul. 30, 1993, Pat. No. 5,610,137, which is a continuation-in-part of Ser. No. 630,825, Dec. 20, 1990, abandoned.

[51] Int. Cl.$^6$ .................................................. C07K 14/805
[52] U.S. Cl. ................................................. 514/6; 530/385
[58] Field of Search ................................ 514/6; 530/385

[56] References Cited

U.S. PATENT DOCUMENTS

| | | | |
|---|---|---|---|
| 4,861,867 | 8/1989 | Estep | 530/385 |
| 5,028,588 | 7/1991 | Hoffman et al. | 514/6 |
| 5,115,100 | 5/1992 | Wu et al. | 530/385 |
| 5,449,759 | 9/1995 | Hoffman et al. | 530/385 |

FOREIGN PATENT DOCUMENTS

| | | |
|---|---|---|
| 6357744 | 11/1990 | Australia . |
| WO 88/03408 | 5/1988 | WIPO . |
| WO 88/09179 | 12/1988 | WIPO . |
| WO 90/13645 | 11/1990 | WIPO . |

OTHER PUBLICATIONS

Gould et al., Annals of Surgery 211:394 (1991).
Behringer et al., Science 245:971 (1989).
Matsumura et al., Proceedings of the National Academy of Science 86:6562–6566 (1989).
Moss et al., Biomat., Art. Cells, Art. Org. 16:57–69 (1988).
Snyder et al., Proceedings of the National Academy of Science 84:7280–7284 (1987).
Bunn et al., W.B. Saunders Co., Philadelphia pp. 13–35 and 381–451 (1986).
Tondo et al., An Acad. Brasil. Cienc. 57:498 (1985).
Nagai et al., Proc. Natl. Acad. Sci. USA 82:7252–7255 (1985).
Bonaventura et al., Science 158:800 (1967).

*Primary Examiner*—Karen C. Carlson
*Attorney, Agent, or Firm*—Clark & Elbing LLP

[57] ABSTRACT

Transgenic, recombinantly cross-linked polymeric human hemoglobins suitable as cell-free blood substitutes have been produced. A plurality of DNA constructs have been designed for efficient expression of modified human hemoglobins in the erythrocytes of the non-human transgenic animals. Substantially pure, non-immunogenic, artificial human hemoglobins are then easily obtained from the erythroid cells of the transgenic animals.

9 Claims, 12 Drawing Sheets

```
                        Ala His Val Asp Cys Met Pro Asn Ala
HS 1-5      5 4 3 2 1  ,CGC ACG TGG ACT GCA TGC CCA ACG C ,  α 75
β 75, 92    ↓ ↓ ↓ ↓ ↓ ─────────────X─────────────────────
5 4 3 2 1              'Ala His Lys Leu Cys Val Asp Pro Val'  α 92
                        GCG CAC AAG CTT TGC GTG GAC CCG GTC

Pro Tro Thr Glu Cys Phe Phe Glu Ser
HS 1-5      5 4 3 2 1  ,CCT TGG ACC CAG TGT TTC TTT GAG TCC,  β 40
β 40, Bovine ↓ ↓ ↓ ↓ ↓ ─────────────X─────────────────────
5 4 3 2 1              '(Non-coding)    Met Leu Thr Pro Glu'  β Bovine
                        CAA ACA GAC ACC ATG CTG ACT CCT GAG Pro Tro Thr Glu Cys Phe Phe Glu Ser
HS 1-5      5 4 3 2 1  ,CCT TGG ACC CAG TGT TTC TTT GAG TCC,  β 40
β 40, Kansas ↓ ↓ ↓ ↓ ↓ ─────────────X─────────────────────
5 4 3 2 1              'Val Asp Pro Glu The Phe Arg Leu Leu'  β Kansas
                        GTG GAT CCT GAG ACC TTC AGG GTG AGT (Non-coding)    Met Leu Thr Pro Glu
            5 4 3 2 1  ,CAA ACA GAC ACC ATG CTG ACT CCT GAG,  β Bovine
HS 1-5       ↓ ↓ ↓ ↓ ↓ ─────────────X─────────────────────
β Bovine, Porto Alegre 'Pro Glu Glu Lys Cys Ala Val Thr Ala'  β Porto Alegre
5 4 3 2 1               CCT GAG GAG AAG TGT GCC GTT ACT GCC Val Aso Pro Glu The Phe Arg Leu Leu
            5 4 3 2 1  ,GTG GAT CCT GAG ACC TTC AGG GTG AGT,  β Kansas
HS 1-5       ↓ ↓ ↓ ↓ ↓ ─────────────X─────────────────────
β Kansas, Porto Alegre 'Pro Glu Glu Lys Cys Ala Val Thr Ala'  β Porto Alegre
5 4 3 2 1               CCT GAG GAG AAG TGT GCC GTT ACT GCC
```

TRANSGENIC, CROSS-LINKED HEMOGLOBIN

This is a divisional of application Ser. No. 08/100,465, filed Jul. 30, 1993, now U.S. Pat. No. 5,610,137, which is a continuation-in-part of application Ser. No. 07/630,825, filed Dec. 20, 1990, now abandoned.

FIELD OF THE INVENTION

The present invention is related generally to the field of recombinant DNA technology. More particularly, the present invention is related to providing transgenic hemoglobins suitable for use as cell free blood substitutes in humans.

BACKGROUND OF THE INVENTION

Ever since blood was recognized as the life-sustaining fluid, and as the science and technology progressed, it has been a goal of human ingenuity to produce an artificial substitute for blood. Toward this goal, Mulder et al. (1934, J. Cell. Comp. Physiol. 5:383–397) used purified human hemoglobin from outdated blood and performed the first experiment for testing the cell-free hemoglobin as a temporary blood substitute. In 1976, Moss et al. (1976, Surg. Gynecol. Obstet. 142:357–362) repeated Mulder et al's supra experiment and confirmed the observation that cell-free hemoglobin could serve as an effective oxygen carrier, although oxygen delivery to tissues was lower than normal.

Several approaches were then taken to solve the problem of altered oxygen affinity of the cell-free hemoglobin. One of the approaches was to covalently attach pyridoxal phosphate to the amino terminus of the $\beta$-globin polypeptide (R. E. Benesch et al., Biochem. 11:3576 (1972); G. S. Moss et al., Surgery 95:249 (1984); L. R. Sehgal et al., Surgery 95:433 (1984)). A second approach was to stabilize the hemoglobin tetramers normally formed in erythrocytes, by chemical crosslinking. (Snyder et al., 1987, Proc. Natl. Acad. Sci. USA 84:7280–7284; Moss et al., 1988. Biomat. Art. Cells, Art. Org. 16:57–69).

Although intramolecular crosslinking significantly improved stability, hemoglobin was detectable in the urine of experimental animals and nephrotoxicity was observed as a side-effect.

Further advance was made when Gould et al. (1990, Ann. Surg. 211394–398) demonstrated that polymerized, pyridoxylated human hemoglobin is well-suited as an efficient oxygen carrier and temporary blood substitute.

Even though these advances are significant, an important limiting factor that must be recognized is that the source of human hemoglobin is blood and human blood is in short supply. Furthermore, the risk of contamination of the blood with such agents as the hepatitis and human immunodeficiency viruses is an omnipresent problem, particularly when large amounts of human blood from a variety of different sources is to be handled in a production-type facility.

Recently Nagai et al. (1985, Proc. Natl. Acad. Sci. USA. 82:7252–7255) and Ryan et al. (1990, Science 245: 971–973) demonstrated an alternative approach by synthesizing human hemoglobin in non-human host by recombinant DNA technology.

SUMMARY OF THE INVENTION

The invention features transgenic, recombinantly cross-linked, polymeric human hemoglobin which exhibits stability and oxygen exchange efficiency sufficient for use as a cell-free blood substitute. Preferably, the polymeric hemoglobin of the invention is a tetramer, octamer, dodecamer, or combination thereof, and is encoded by a DNA molecule including a recombinantly-introduced cysteinyl residue which facilitates formation of an intramolecular or intermolecular disulfide bridge, or both. Linkage of two or more tetramers via disulfide bridges is of particular importance because the increased molecular size provided by such linkage minimizes filtration by the kidneys, which can occur with molecules the size of tetramers or smaller. The disulfide bridge which can be formed by virtue of the recombinantly introduced cysteinyl residue preferably is between one or more of (a) $\alpha$1 92 to $\beta$2 40; (b) $\beta$1 1 to $\beta$2 146; or (c) $\alpha$1 130 to a cysteinyl residue added to the carboxy terminus of $\alpha$2 142.

The hemoglobin of the invention is preferably encoded by a pair of recombinant DNA molecules in which the first molecule encodes a first human hemoglobin chain in a non-human transgenic animal, and the second recombinant molecule encodes a second, different human hemoglobin chain in the animal, such that when a complete human hemoglobin is formed in red blood cells and when this hemoglobin is isolated in substantially pure form and incubated at about 4° C. under conditions which allow oxidation of the protein moiety of the hemoglobin without oxidation of the heme groups present in the hemoglobin, a stable, polymeric hemoglobin molecule is obtained without need for further chemical modification of the hemoglobin.

The invention provides stable polymeric human hemoglobin which possesses oxygen exchange characteristics sufficiently close to natural hemoglobin to enable its use in human patients as a cell-free blood substitute.

In one class of recombinant mutant human hemoglobin molecules of the invention there are two mutations, the first of which causes an increase in oxygen affinity, and the second of which causes a balancing decrease in oxygen affinity, such that the net result is a lowering of the oxygen affinity of the molecule compared to naturally-occurring human hemoglobin, i.e., the oxygen affinity decreasing mutation has a greater effect than the oxygen affinity increasing mutation. Preferably, the oxygen affinity of the recombinant molecule is 75 to 90% that of the naturally-occurring molecule. The mutation which causes an increase in oxygen affinity preferably involves the introduction of a cysteinyl residue for the formation of a disufide bridge.

Other features and advantages of the invention will be apparent from the following description of the preferred embodiments thereof, and from the claims.

DETAILED DESCRIPTION

The drawings are first described.

Genetically Modified Hemoglobin

The above and various other objects and advantages of the present invention are achieved by genetically modified, recombinant, transgenic, human hemoglobin molecule having a degree of stability and oxygen exchange efficiency, without chemical cross-linking, similar to the hemoglobin molecule in the whole blood, and by DNA constructs for synthesizing the molecule in non-human transgenic animals.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantially pure" as used herein means as pure as can be obtained by standard isolation and purification techniques known in the art to which this invention relates.

The term "recombinantly modified" as used herein means that the genetic makeup of the molecule has been modified by recombinant DNA technology including site-directed mutagenesis and the like, and not by chemical treatment of the molecule.

The term "transgenic" as used herein means that the molecule is obtained from transgenic animals expressing the modified human hemoglobin genes as described more fully herein infra. The molecular modification required for the formation of disulfide bridges to produce stable polymeric hemoglobins (tetramers or higher molecular weight aggregates) are introduced in the hemoglobin gene through recombinant genetic means and not through conventional chemical cross-linking techniques.

The term "human hemoglobin molecule" as used herein means a molecule whose amino acid sequence at least in part corresponds to the amino acid sequence of a naturally-occurring human hemoglobin molecule, whether mutated or unmutated.

Human hemoglobins with intramolecular disulfide crosslinks

It has been found that hemoglobin tetramers rapidly dissociate into $\alpha\beta$ dimers when red cells are lysed and the concentration of hemoglobin is decreased by dilution. To prevent tetramers from dissociating, the present invention identifies several sites for introducing internal, disulfide crosslinks into human hemoglobin. These crosslinks stabilize $\alpha_2\beta_2$ tetramers and, therefore, prolong the half-life of cell-free hemoglobin. The crystal structure of both deoxy- and oxy-hemoglobin have been accurately determined and the important sites of subunit interaction are known. The atomic distances were examined between various amino acids in areas of subunit interaction and several sites were identified in which cysteine substitutions for the normal amino acids in $\alpha$ and $\beta$ polypeptides result in the formation of disulfide bridges between these chains. Those sites which would allow bond angles that favor disulfide linkage were chosen for mutagenesis.

Stabilization of human hemoglobin tetramers requires disulfide crosslinks between the two $\alpha\beta$ dimers. Crosslinks could be between the $\alpha 1$ and $\beta 2$ subunits, the $\alpha 1$ and $\alpha 2$ subunits, or the $\beta 1$ and $\beta 2$ subunits. Computer-assisted modeling and energy minimization were utilized to identify the sites in which cysteine substitutions for the normal amino acids would lead to the most stable disulfide bridges. The most stable tetramer disulfide bridges thus determined include from:

1) $\alpha 1$ 92 to $\beta 2$ 40
2) $\beta 1$ 1 to $\beta 2$ 146
3) $\alpha 2$ 130 to a cysteine added to the carboxy terminus of the $\alpha 1$ chain, designated $\alpha 1$ 142.

Figure 1:
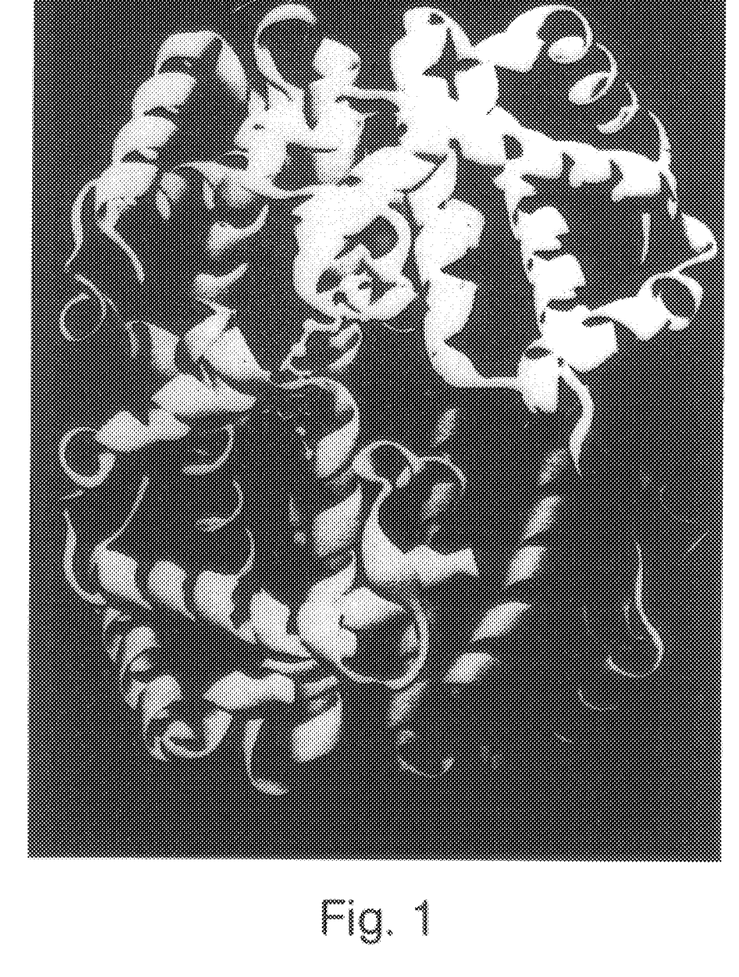
FIG. 1 illustrates the $\alpha$92–$\beta$40 tetramer crosslinks.

Of the above disulfide bridges, a preferred one is $\alpha 1$ 92 to $\beta 2$ 40 or $\alpha 2$ 92 to $\beta 1$ 40 crosslink because a disulfide in this position would not hinder the rotations of $\alpha\beta$ dimers with respect to each other during the cooperative binding of oxygen. FIG. 1 illustrates the $\alpha 92-\beta 40$ tetramer crosslinks. The yellow balls represent sulfur atoms involved in disulfide crosslinks.

Intermolecular Disulfides for Polymerization of Hemoglobin Tetramers

In addition to stabilizing the tetramer, disulfide bridges can also be used to link tetramers together to form polymers, such as octomers and the like. Tetramers stabilized by chemical crosslinking have a half-life of only 4 hours in vivo. Although the tetramers have a molecular weight of 64,000, they are filtered by the kidneys and can cause renal damage. Linkage of 2 tetramers produces a molecule of about 128,000 daltons. It has been demonstrated that octomers and higher molecular weight polymers produced by chemical crosslinking have a half-life of 40–48 hours in vivo and these molecules are not filtered by the kidneys. (Gould et al. (1990), Ann. Surg. 211:394–398).

Figure 2:
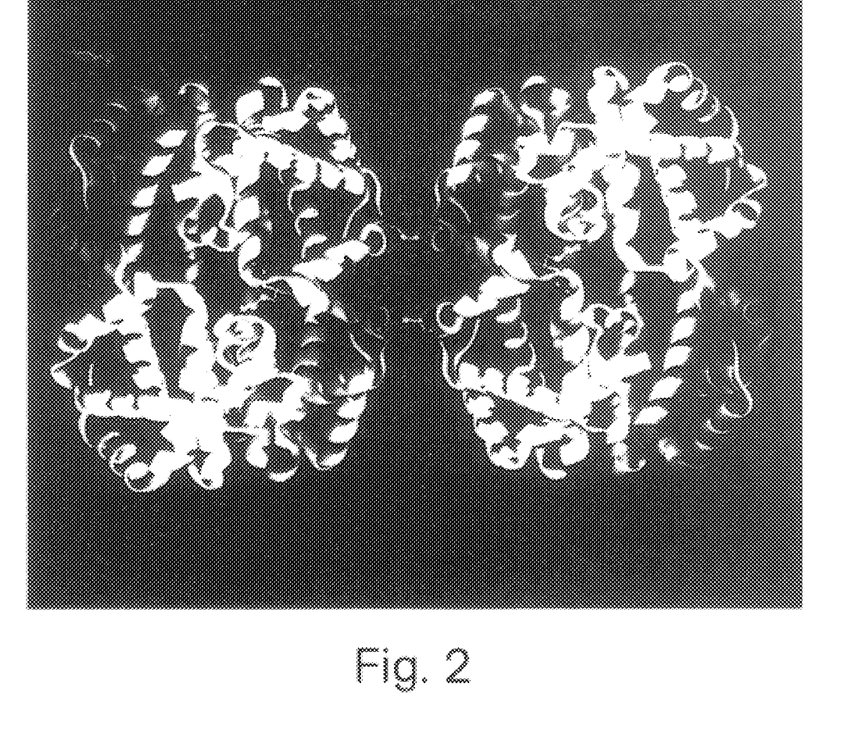
FIG. 2 illustrates the octomer mutation and $\alpha$1–$\beta$2 tetramer crosslinkage.

Another important advantage of polymerization of the hemoglobin relates to the osmotic property of the polymer. The highest concentration of a crosslinked tetramer that would be iso-osmotic is 7 g/dl. However, this concentration does not provide sufficient oxygen carrying capacity (Gould et al. (1990), Ann. Surg. 211:394–398). An octomeric polymer would be iso-osmotic at 14 g/dl which is the physiologic hemoglobin concentration. Hence, the crystal structures of deoxy-and oxy-hemoglobin were examined to determine the best position for a disulfide bridge between 2 tetramers. It was found that changing the a1 aspartic acid 75 to cysteine would produce a molecule capable of forming intermolecular crosslinks. Once an octomer is formed, steric hindrances inhibit further polymerization. FIG. 2 illustrates the octomer mutation and $\alpha 1-\beta 2$ tetramer crosslinkage. Yellow balls represent sulfur atoms involved in disulfide crosslinks.

Alternative Self-Limiting Polymerization Strategy

As an alternative to the polymerization strategy described above, a naturally-occurring mutation which also results in polymerization was examined. This mutation is known as Hemoglobin Porto Alegre and involves a change from serine to cysteine at position 9 of the beta chain (Tonda et al., 1963, Amer. J. Human Genetics 15 265–279; Bonaventura and Riggs, 1967, Science 158: 800–802).

Hemoglobin (Hb) Porto Alegre polymerizes in a self-limiting fashion to form octamers composed of two hemoglobin tetramers or dodecomers composed of three tetramers (Bonaventura and Riggs, supra; Tonda, 1971, An. Acad. brasil. Cienc 43: 651–669). Although this hemoglobin does not polymerize in vivo, it forms stable polymers in vitro after exposure to gentle oxidizing conditions. After polymerization in vitro, polymers of Hb Porto Alegre are stable in reducing conditions similar to serum (Tonda et al., 1985, An. Acad. brasil. Cienc. 57: 497–506). Therefore, it was postulated that genetically modified polymers would be ideally suited to function as a blood substitute. One undesirable characteristic of Hb Porto Alegre, however, is its increased oxygen affinity. In order to overcome this limitation, a second, oxygen affinity decreasing mutation can be made, as described below.

Approximation of Normal Oxygen Affinity in Hemoglobin Porto Alegre

The oxygen affinity of human hemoglobin is regulated by the molecule 2,3-diphosphoglycerate (DPG). Outside of red blood cells, DPG diffuses away from hemoglobin, resulting in a large increase in the hemoglobin's oxygen affinity. The present invention provides for a unique solution to the loss of DPG regulation. This is accomplished by modification of the human hemoglobin so that its oxygen affinity will approximate that of bovine hemoglobin.

Figure 3:
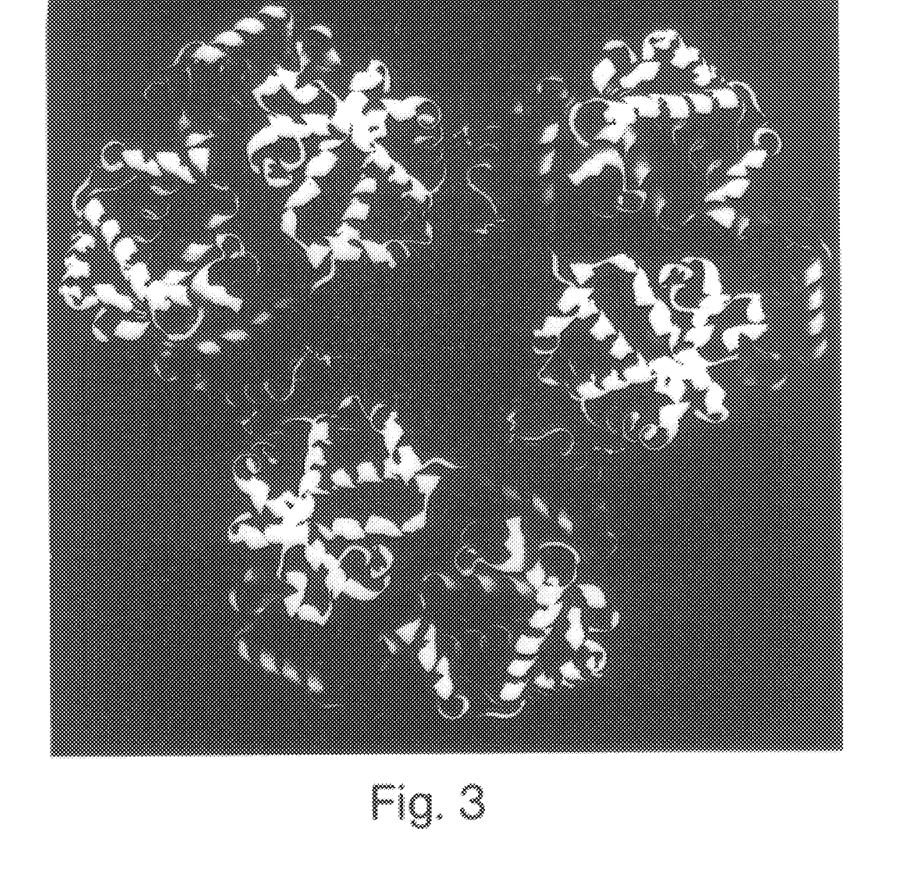
FIG. 3 illustrates the dodecamer containing bovine and Porto Alegre mutations.
Figure 4A:
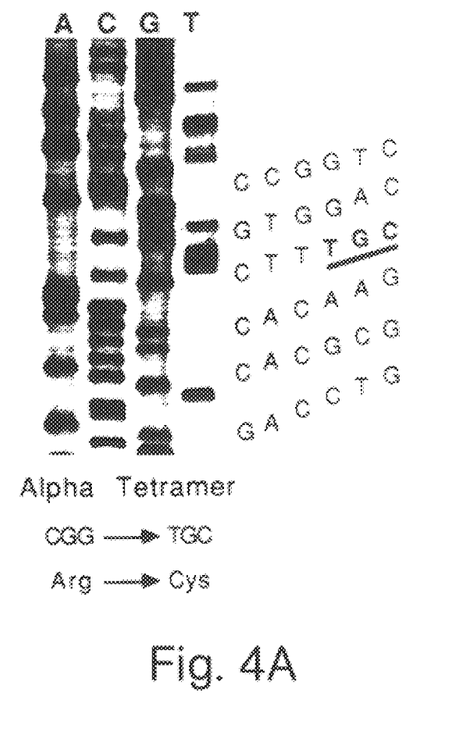
FIGS. 4A–4F illustrate the nucleotide sequences (panels A–F) of various mutations created in accordance with the present invention and employed to synthesize the mutant hemoglobins.
Figure 4B:
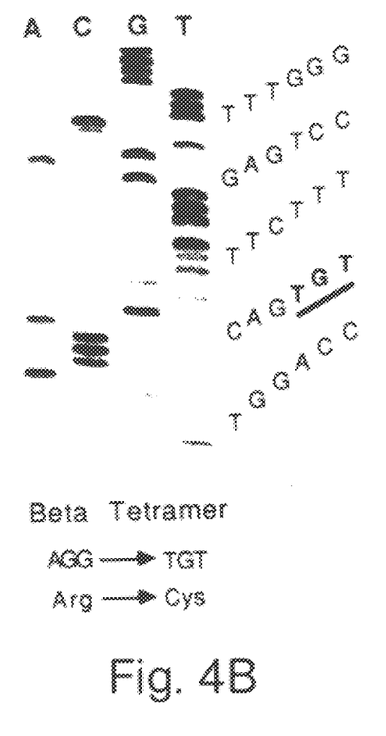
Figure 4C:
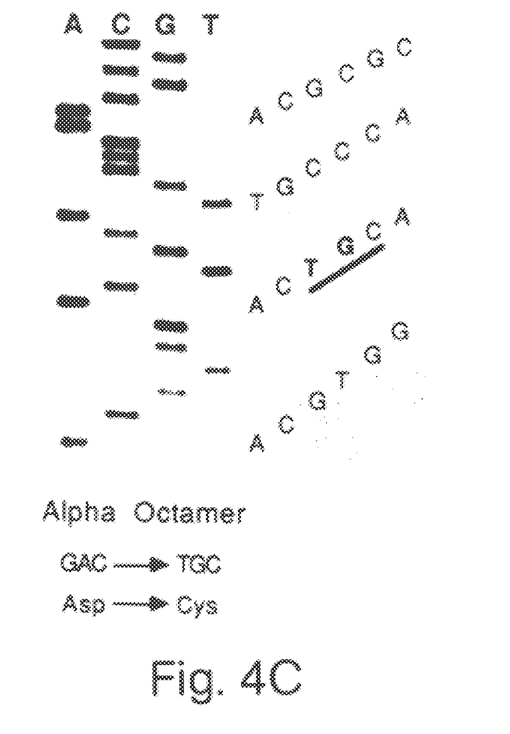
Figure 4D:
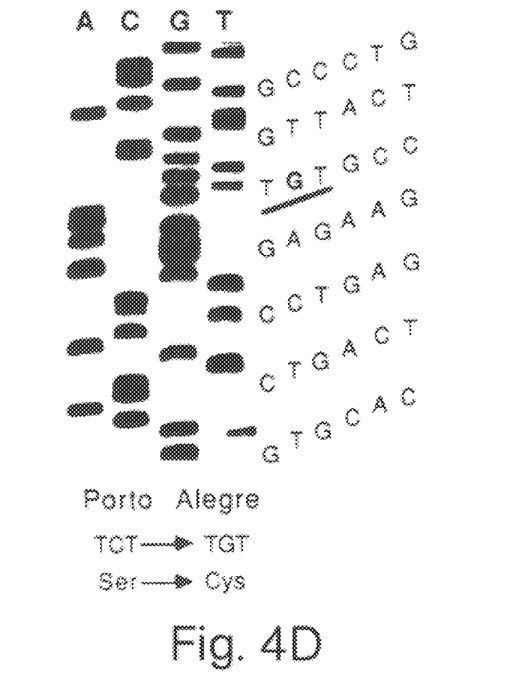
Figure 4E:
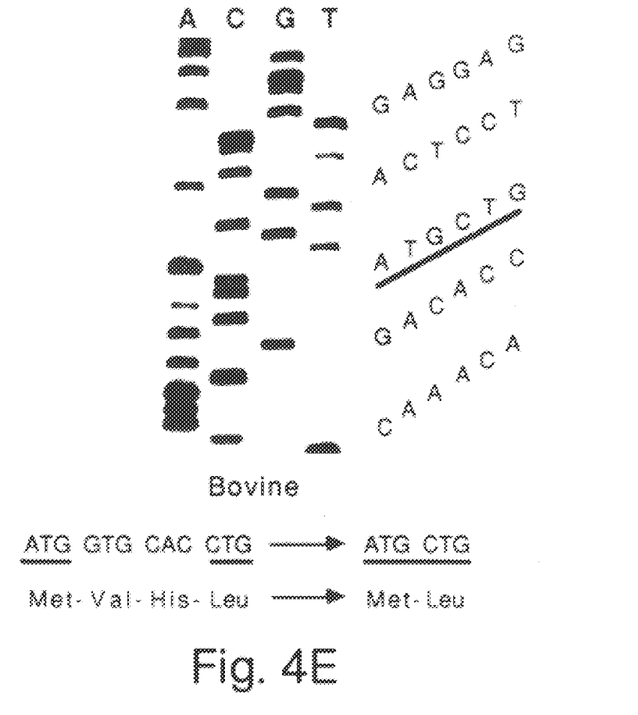
Figure 4F:
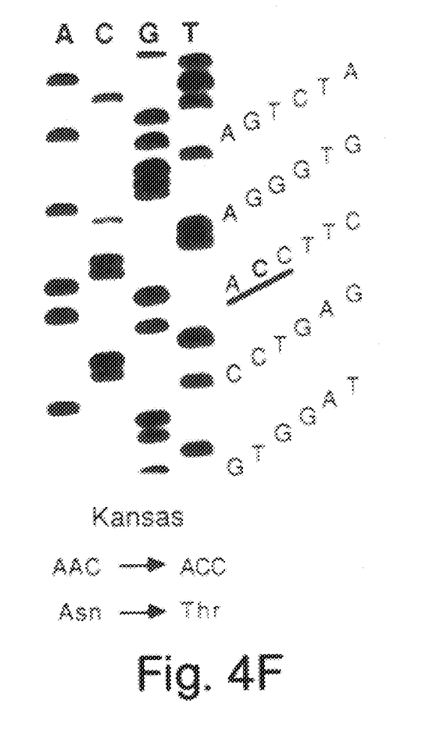
Figure 5:
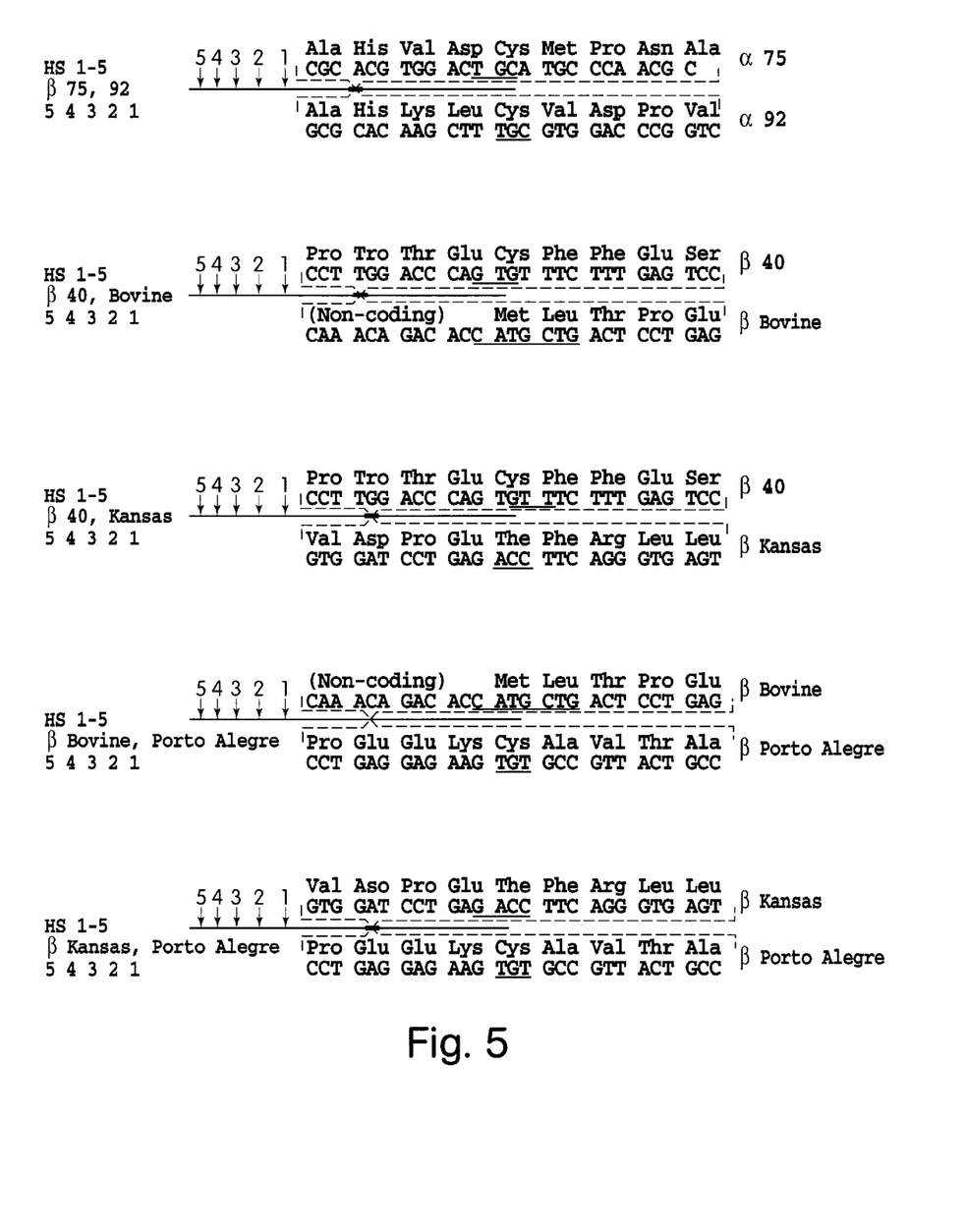
FIG. 5 illustrates the maps of cosmid constructs used for microinjection.

Bovine hemoglobin has a naturally low oxygen affinity which is not dependent upon DPG. Perutz and Imai (1980, J. Mol. Biol. 136: 183–191) characterized the amino acid change responsible for the decreased oxygen affinity of bovine hemoglobin. The change occurs at the amino terminus of the beta chain and involves the replacement of a hydrophilic residue at position NA2 with a hydrophobic residue. The present invention involves the removal of the first two amino acids at the N-terminus of the beta chain and their replacement by the hydrophobic amino acid methionine. The resulting $\beta$-globin polypeptide is composed of 145 amino acids instead of 146 and mimicks the bovine $\beta$-globin chain at the amino terminal end. FIG. 3 illustrates a computer model of the dodecamer containing the bovine and Porto Alegre mutation.

As mentioned above, the invention also provides for a second mutation, designed to counteract the increase in oxygen affinity of Hb Porto Alegre. One such mutation, which occurs naturally, is known as Hb Kansas. In Hb Kansas the beta 102 asparagine is changed to threonine (Bonaventura and Riggs, 1968, J. Biol. Chem. 243: 980–991). This mutation stabilizes the T or Tense conformation of hemoglobin which is the structure normally found in venous blood after oxygen has been delivered to the tissues. The oxygen affinity of Hb Kansas is 2 fold lower than normal HbA. Therefore, it was postulated that Hb Kansas may decrease the abnormally high affinity associated with Hb Porto Alegre. Hence, combinations of Hb Porto Alegre and Hb Kansas as well as Hb Porto Alegre and the bovine mutations were constructed. The present invention provides for these unique combinations of mutant hemoglobins and for their use as blood substitutes.

Other Genetic Modification of Human Hemoglobins Synthesized in Transgenic Animals As described above, the present invention provides for the genetic modifications of human hemoglobin, but is not limited to these specific examples. Computer-assisted modeling and energy minimization were employed to identify the sites in which cysteine substitutions for the normal amino acids would lead to the most stable disulfide bridges. Of course, following this strategy any number of new designs of these hemoglobin molecules can be generated. The basic strategy for identifying sites for cysteine substitution is as follows. The molecular coordinates of hemoglobin obtained from the Brookhaven Data Bank were loaded into an Evans and Sutherland PS300 Computer Graphics System. Cysteine substitutions were made at a variety of positions. Bond angles between pairs of cysteine residues on $\alpha$1 and $\beta$2 chains were adjusted such that $\beta$ carbon atoms were separated by less than 3.5 angstroms and disulfide bonds were formed between these residues. The disulfide linked tetramer was then subjected to energy minimization as described by Powell (1977, Mathematical Programing 12, 241–254) on a silicon graphics IRIS-4D. Briefly, energy minimization was conducted using the Powell-method conjugate gradient minimizer provided in the software system X-PLOR version 2.1 (Brunger, 1990, X-PLOR: A System for Crystallography and NMR, Yale University, New Haven). Twenty-five hundred cycles of minimization were conducted using both the oxy- and deoxyhemoglobin molecular coordinates. This established a baseline minimal total energy to which hemoglobins with engineered disulfides could be compared. The engineered hemoglobin with a disulfide bond from $\alpha$1 92 to $\beta$2 40 displayed energy minima which were similar to those of the native human hemoglobin in both the deoxy- and oxygenated conformations. This bridge was subsequently selected as the first disulfide for tetramer stabilization to be engineered by site-directed mutagenesis. Specific cysteine codons were then introduced into $\alpha$- and $\beta$- globin genes by site specific mutagenesis. Furthermore, experimental data obtained from transgenic animals may suggest additional modifications to be incorporated into the design. Thus, the present invention provides for any mutant hemoglobin synthesized in transgenic animals for use as a blood substitute including a combination of naturally occurring mutants with those specifically designed by computer modeling and site-directed mutagenesis and the like.

Various embodiments illustrative of the inventions are now set forth.

EXAMPLE 1

Mutagenesis of Human $\alpha$- and $\beta$-globin Genes

Mutations were introduced into the normal human $\alpha$- and $\beta$-globin genes by site-directed mutagenesis. A 3.8 kb BglII-EcoRI fragment containing the human $\alpha$-globin gene and a 4.1 kb HpaI-XbaI fragment containing the human $\beta$-globin gene were cloned into the pSELECT plasmid (Lewis and Thompson, (1990, Nucl. Acids Res. 18: 3439–3443) by standard procedures (Maniatis et al., 1989, Molecular Cloning; A Laboratory Manual, Cold Spring Harbor Laboratory, Cold Spring Harbor, N.Y.). Oligonucleotide mutagenesis was performed as described by Lewis and Thompson, 1990, Nucl. Acids Res. 18: 3439–3443. In this procedure an oligonucleotide which corrects a mutation in the ampicillin resistance gene in the pSELECT plasmid is used simultaneously with one or more oligonucleotides designed to create mutations in the globin gene insert. Briefly, *E. coli* (JM109) containing the pSELECT plasmid with globin gene inserts were infected with helper phage (M13K07). After growing the culture overnight (about 12–16 hours), phage obtained from the supernatant were extracted with phenol:chloroform and single-stranded DNA was isolated by standard methodology. Oligonucleotides containing each of the mutations were annealed to single-stranded DNA together with the wild type ampicillin oligonucleotide and these primers were extended with Klenow for about 90 min. at 37° C. Double-stranded DNA was transformed into *E. coli* (BMH 71-18 mutS) and the culture was grown overnight in L broth containing 75 $\mu$g/ml ampicillin. DNA obtained from rapid lysis preparations of these cultures were transfected into *E. coli* (JM109) and colonies were selected on ampicillin plates (75 $\mu$g/ml). Double-stranded DNA obtained from rapid lysis preparations of these colonies was sequenced (Sanger et al., 1977, Proc. Natl. Acad. Sci. USA 74: 5463–5467) with oligonucleotides located upstream of the mutagenic oligonucleotides. Mutants were clearly identified by comparison to wild type sequence. The oligonucleotides used to generate the mutations include those listed below. Underlined bases indicate the bases which differ from the wild type.

I. Tetramer intramolecular crosslink
   A. α92 arginine to cysteine
      CGG to TGC
      5' GCGCACAAGCTT
      TGCGTGGACCCGGTC3'(SEQ ID NO: 1)
   B. β40 arginine to cysteine
      AGG to TGT
      5' CCTTGGACCCAGTGTTTCTTTGAGTCC3'(SEQ ID NO: 2)
II. Polymerization intermolecular crosslinks
   A. α75 aspartic acid to cysteine (α octamer)
      GAC to TGC
      5' CGCACGTGGACTGCATGCCCAACGC3'(SEQ ID NO: 3)
   B. β9 serine to cysteine (Porto Alegre)
      TCT to TGT
      5' CCTGAGGAGAAG
      TGTGCCGTTACTGCC3'(SEQ ID NO: 4)
III. Mutations to lower oxygen affinity
   A. β102 asparagine to threonine (Hb Kansas)
      AAC to ACC
      5' GTGGATCCTGAG
      ACCTTCAGGGTGAGT3'(SEQ ID NO: 5)
   B. Bovine mutation (βΔ1–2) in which the first and second codons, GTG (valine) and CAC (histidine), are deleted
      5' CAAACAGACACC
      ATGCTGACTCCTGAG3'(SEQ ID NO: 6)
   The wild type DNA sequence is ATG GTG CAC CTG ACT (SEQ ID NO: 7) and the mutated sequence is ATG CTG ACT (SEQ ID NO: 8). The wild type amino acid sequence is Met-Val-His-Leu-etc. The methionine is cleaved from the amino terminal end by an aminopeptidase and the final protein is composed of 146 amino acids. The amino acid sequence of the mutant is Met-Leu-etc. The methionine is not removed from the amino terminal end because the aminopeptidase does not cleave the Met-Leu peptide bond. The final protein is thus composed of 145 amino acids.

The α75 and α92 mutations were introduced simultaneously into the α-globin gene with two separate oligonucleotides. The β40 and Bovine (βΔ1–2) mutations were introduced into the β-globin gene in a single mutagenesis with 2 different β-globin oligonucleotides. Similarly, the β40 and Kansas mutations were also introduced in the β-globin gene in a single mutagenesis with 2 different β-globin oligonucleotides. The Porto Alegre (β9) and Hb Kansas (β102) mutations were also introduced into the β-globin gene in a single mutagenesis with 2 different β-globin oligonucleotides. The Porto Alegre and bovine (βΔ1–2) mutations were created with a single 48 base oligonucleotide. The nucleotide sequences of α75 (FIG. 4C), α92 (FIG. 4A), β9 (Porto Alegre) (FIG. 4D), β40 (FIG. 4B), β102 (Kansas) (FIG. 4F) and βΔ1–2 (Bovine) (FIG. 4E) mutations are shown in FIG. 4, panels A–F.

EXAMPLE 2
Construction of Cosmid Clones

Mutant α- and β-globin genes were excised from pSELECT plasmids and subcloned into "right arm" plasmids containing a Cos site. Specifically, a 1.2 kb NcoI-XbaI fragment from the α-globin pSELECT plasmids and a 1.4 kb ClaI-BamHI fragment from the β-globin pSELECT plasmids were inserted into right arm plasmids in place of the corresponding α- and β-globin gene wild type fragments. The α-globin right arm plasmids were digested with ClaI and MluI and 4.8 kb fragments containing mutated α-globin genes which were linked to Cos sites were purified from agarose gels. The β-globin right arm plasmids were digested with ClaI and HindIII and 6.5 kb fragments containing mutated β-globin genes which were linked to Cos sites were purified from agarose gels. Cosmids containing these fragments were constructed in four way ligations (Ryan et al., 1989, Genes. Dev. 3: 314–323). The left arms were 9.0 kb MluI-SalI fragments obtained from the cosmid vector pCV001 (Lau and Kan, 1983, Proc. Natl. Acad. Sci. U.S.A. 80: 5225–5229). This fragment contained a Cos site, an ampicillin resistance gene, a ColE1 origin and the SVneo gene. The two internal fragments were a 10.7 kb SalI-KpnI fragment containing DNase I super-hypersensitive (HS) sites V, IV and III and a 10.9 kb KpnI-ClaI fragment containing HS II and I. The four fragments were ligated together in a 2:1:1:2 molar ratio of vector arms to inserts and packaged (Packagene; Promega). E. coli ED8767 was infected with the packaged cosmids and plated onto ampicillin plates. Large scale cultures of ampicillin resistant colonies were grown and cosmids were prepared by standard procedures.

EXAMPLE 3
Production of Transgenic Animals

Cosmid DNA was prepared by standard procedures. HS I-V α and HS I-V β cosmids containing the mutations described above were injected directly into fertilized mouse eggs or the constructs were digested with SalI and insert DNA was separated from plasmid DNA by agarose gel electrophoresis before injection. The eggs were injected and transferred to pseudopregnant foster mothers (Brinster et al., 1985, Proc. Natl. Acad. Sci. USA 82: 4438–4442) and transgenic progeny were identified by Southern blot hybridization of tail DNA. Similarly, large animal eggs can be injected with the same constructs and transferred to foster mothers as described by Pursel et al. (1989, Science 244: 1281–1288).

Typically, human α- and β-globin genes were cloned into expression vectors designed to direct high levels of α- and β-globin synthesis in erythroid cells of transgenic animals. These constructs were coinjected into fertilized mouse eggs and expression was analyzed in transgenic animals that developed. All of the mice that contained intact copies of the transgenes expressed correctly initiated human α- and β-globin MRNA specifically in erythroid tissue. Isolectric focusing of hemolysates demonstrated that a complete human hemoglobin was formed in adult erythrocytes and oxygen equilibrium curves of human hemoglobin purified from these mice demonstrated that the molecule was fully functional. The animals are healthy and faithfully transmit the human genes to progeny. These animals have been bred for over 20 generations and the progeny continue to synthesize equal amounts of human and mouse hemoglobins.

It is pointed out that similar methodology can be used to produce functional (capable of efficiently delivering oxygen to tissues) human hemoglobin in large animals, such as pigs, sheep, goats, cows and the like.

EXAMPLE 4
Analysis of Blood from Transgenic Animals

Blood collected from transgenic animals is washed with saline and hemolysates prepared as described by Ryan et al., 1990, Science 245: 971–973. Hemoglobin is analyzed on isoelectric focusing (IEF) gels (Ryan et al., 1990, supra). Human hemoglobin bands are excised from IEF gels and analyzed on urea cellulose acetate strips to demonstrate that the human hemoglobin band is composed of human α- and β-globin polypeptides. It is noted that if human hemoglobin is difficult to separate from endogenous hemoglobins, mutations that increase or decrease the isoelectric point (pI) of human hemoglobin can be introduced into the α- and β-globin genes. Increases in pI are accomplished by introducing basic (positively charged) amino acids into the protein and decreases are accomplished by introducing acidic (negatively charged) amino acids. These charged amino acids are introduced at positions which do not disturb the structure or function of the protein. Oxygen equilibrium curves of purified hemoglobin are then determined as described by Ryan et al. (1990, supra).

EXAMPLE 5
Formation of Disulfide Crosslinks

Disulfide crosslinks in proteins are not easily formed inside erythrocytes because high concentrations of glutathione prevent oxidation (Tondo et al., 1985 supra). Both intramolecular and intermolecular disulfide crosslinks are formed after human hemoglobin is purified by isoelectric focusing as described above. Large scale purifications are accomplished by chromatofocusing (Giri, 1990, Methods. Enzymol., 182: 380–392) which also separates proteins according to their isoelectric focusing points. Purified human hemoglobin is then incubated for several days at 4° C. in slightly alkaline conditions (0.1M Tris-HCL pH 8.0; Matsumura et al., 1989, Proc. Natl. Acad. Sci. USA 86: 6562–6566) to gently oxidize the protein without oxidizing heme groups. Crosslinked hemoglobins are dialysed into phosphate buffered saline at pH 7.5 by tangential flow ultrafiltration (Shiloash et al., 1988, Adv. Biotechnol. Processes 8: 97–125) against membranes which retain polymers greater than 100,000 MW. These purified proteins are then analyzed on reducing and non-reducing olyacrylamide gels. Also, the oxygen equilibrium curves of these samples are obtained. Finally, the hemoglobins are tested for oxygen carrying capacity in animals following standard procedures well known in the art.

It is noted that since the transgenically produced human hemoglobin of the present invention is isolated in substantially pure form free of any cellular or subcellular component, it is non-immunogenic; hence, useful as a blood-substitute without the need for blood typing which becomes necessary if the whole blood or red blood cells (RBCs) are to be used. In addition, being of animal origin, the transgenic hemoglobin of the present invention would also be free of such viruses as HIV.

A composition in accordance with the present invention comprises a biologically functional amount (i.e., capable of effective oxygen exchange with the tissues) or a blood substituting amount of the substantially pure transgenic human hemoglobin and a pharmaceutically acceptable vehicle such as physiological saline; non-toxic, sterile buffered medium; human plasma and the like.

The availability of the substantially pure, cell-free, non-immunogenic, biologically functional, non-toxic, polymeric, transgenic human hemoglobin of the present invention now provides a method for supplementing the oxygen exchange capacity of the red blood cells (RBCs) by substituting the RBCs or the naturally occurring (wild type) whole blood with the purified transgenic hemoglobin of the present invention. The recombinant hemoglobin of the present invention is particularly suitable, at least as a temporary substitute, for providing oxygen to tissues during critical times, such as during emergency surgery or until whole blood transfusions can be given, or for entirely obviating the need for whole blood transfusions. Of course, it can also be employed for organ perfusion and the like.

EXAMPLE 6
Production of Transgenic Kansas/Porto Alegre Hemoglobin

Figure 6:
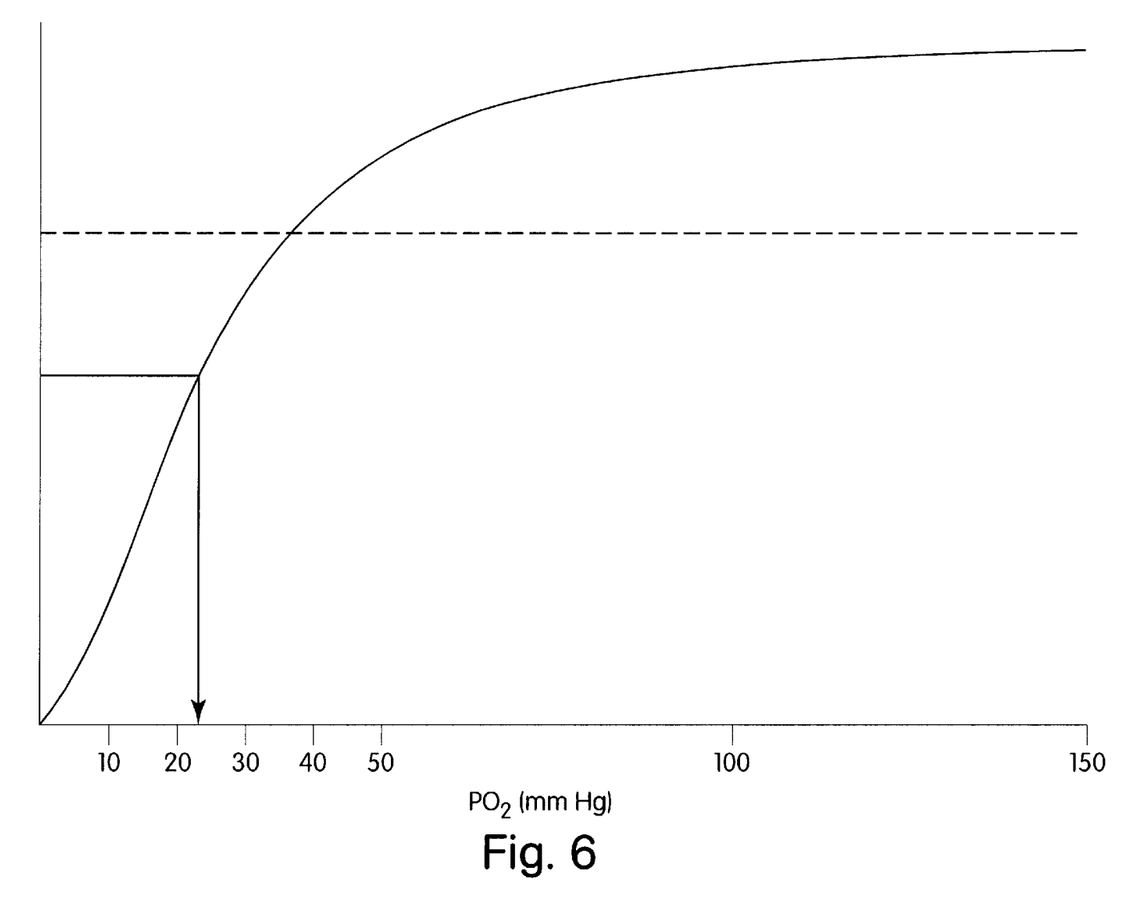
FIG. 6 illustrates an HPLC chromatogram of Kansas/Porto Alegre hemoglobin in transgenic mice.
Figure 7:
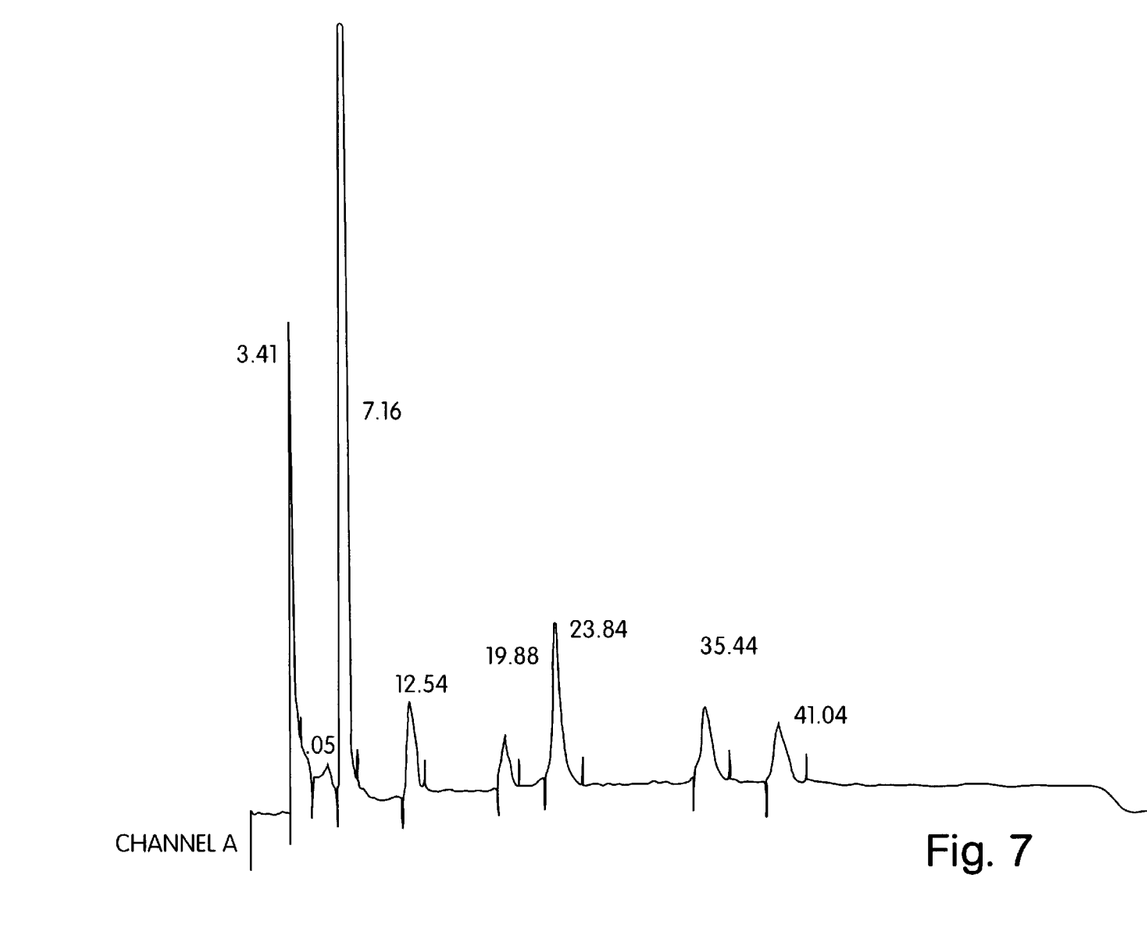
FIG. 7 illustrates an oxygen equilibrium curve of Kansas/Porto Alegre hemoglobin in transgenic mice.

Kansas and Porto Alegre mutations were introduced into the beta chain of human hemoglobin and expression constructs were produced as described above. These expression constructs were introduced into mice also as described above to produce transgenic animals expressing this mutant hemoglobin. Evidence presented in FIG. 6 demonstrates that each chain of the human and mouse hemoglobins is expressed and is stable in vivo. This figure shows the results of standard hemoglobin isolation from the animals followed by anion exchange high performance liquid chromatography under denaturing conditions. Peaks corresponding to each hemoglobin chain: mouse alpha (i.e., both alpha$^1$ and alpha$^4$ isoforms), mouse beta, human alpha, and human beta (containing the Kansas and Porto Alegre mutations) are shown. The HPLC chromatogram demonstrates that 34% of the total β-globin content of the animals is human Kansas/Porto Alegre β-globin, and 41% of the total α-globin is human α-globin. FIG. 7 depicts an oxygen affinity curve (generated by standard techniques) from the blood of the Kansas/Porto Alegre mice (i.e., 40% human/60% mouse hemoglobin). The total hemoglobin in Kansas/Porto Alegre transgenic mice exhibits a $P_{50}$ of 23.5 mm Hg. This value may be compared to normal mouse hemoglobin (13 mm Hg), Porto Alegre hemoglobin (6 mm Hg), Kansas hemoglobin (36 mm Hg), and normal human hemoglobin (10 mm Hg) under similar conditions (0.1M phosphate, pH 7.0; 20° C.). Under physiological conditions, the presence of 2,3-diphosphoglycerate (DPG) in intact red blood cells raises the $P_{50}$ of normal human hemoglobin to 25. The cell-free hemoglobin used for a blood substitute will function in the low DPG environment of the serum. Therefore, the $P_{50}$ of genetically modified hemoglobin should be in the range of 25–35. Both the $P_{50}$ of the transgenic Kansas/Porto Alegre hemoglobin and the fact that viable transgenic offspring are produced indicates that this mutant hemoglobin properly binds oxygen and delivers it to tissues, and thus is functional in vivo.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A transgenic, recombinantly produced, polymeric human hemoglobin molecule having a recombinantly-introduced cysteinyl residue which forms an intramolecular disulfide bridge, said disulfide bridge being formed between β1 1 to β2 146.

2. A transgenic, recombinantly produced, polymeric human hemoglobin molecule having a recombinantly-introduced cysteinyl residue which forms an intramolecular disulfide bridge, said disulfide bridge being formed between α1 130 to a cysteinyl residue added to the carboxy terminus of α2 142.

3. A transgenic, recombinantly produced, polymeric human hemoglobin molecule having a recombinantly-introduced cysteinyl residue which forms an intermolecular disulfide bridge, said cysteinyl residue being introduced by replacing α1 aspartic acid 75 with cysteine or by replacing β9 serine with cysteine.

4. The molecule of claim 1 or 2, further comprising an amino acid substitution which includes the Hemoglobin Porto Alegre mutation in the β chain at Ser9Cys.

5. The molecule of claim 3, further comprising an amino acid sequence which includes the Hemoglobin Kansas mutation in the β chain at Asn102Thr.

6. The molecule of claim 3, further comprising replacing the two amino-terminal β-chain amino acids with methionine or another hydrophobic amino acid.

7. A transgenic, recombinantly produced human hemoglobin molecule comprising the Hemoglobin Kansas mutation in the β chain at Asn102Thr and the Hemoglobin Porto Alegre mutation in the β chain at Ser9Cys.

8. A transgenic, recombinantly produced human hemoglobin molecule comprising two or three polymerized hemoglobin tetramers, each said tetramer having the Hemoglobin Porto Alegre mutation in the β chain at Ser9Cys and replacing the two amino-terminal β-chain amino acids with methionine or another hydrophobic amino acid.

9. A method for supplementing the oxygen-carrying capacity of naturally-occurring whole blood in a mammal comprising administration to said mammal of the hemoglobin molecule of any one of claims 1, 2, 3, 4, 5, 6, 7, or 8.

* * * * *